(12) United States Patent
Liu et al.

(10) Patent No.: US 11,561,308 B2
(45) Date of Patent: Jan. 24, 2023

(54) METHOD FOR MEASURING RADIATION INTENSITY

(71) Applicant: NEUBORON MEDTECH LTD., Jiangsu (CN)

(72) Inventors: Yuan-hao Liu, Jiangsu (CN); Jui-fen Chen, Jiangsu (CN); Jing He, Jiangsu (CN); Ming-chen Hsiao, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 704 days.

(21) Appl. No.: 16/569,931

(22) Filed: Sep. 13, 2019

(65) Prior Publication Data
US 2020/0003910 A1 Jan. 2, 2020

Related U.S. Application Data

(63) Continuation of application No. PCT/CN2018/100729, filed on Aug. 16, 2018.

(30) Foreign Application Priority Data

Aug. 18, 2017 (CN) .......................... 201710710968.7

(51) Int. Cl.
*G01T 1/02* (2006.01)
*G01N 33/68* (2006.01)
*A61N 5/10* (2006.01)

(52) U.S. Cl.
CPC ............ *G01T 1/02* (2013.01); *G01N 33/6803* (2013.01); *A61N 5/10* (2013.01); *A61N 5/1071* (2013.01); *A61N 2005/109* (2013.01)

(58) Field of Classification Search
CPC .................. G01T 1/02; G01N 33/6803; G01N 2333/765; A61N 5/10; A61N 5/1071; A61N 2005/109; A61N 5/1075; A61N 5/1048

See application file for complete search history.

(56) References Cited

U.S. PATENT DOCUMENTS

| 4,039,834 | A | * | 8/1977 | Lucas | G01T 1/11 252/301.4 H |
| 4,506,157 | A | * | 3/1985 | Keller | G01T 1/11 600/436 |

(Continued)

FOREIGN PATENT DOCUMENTS

| CN | 101184998 A | 5/2008 |
| CN | 101975964 A | 2/2011 |

(Continued)

OTHER PUBLICATIONS

Ye Hongping, (Simultaneous determination of protein aggregation, degradation, and absolute molecular weight by size exclusion chromatography-multiangle laser light scattering); Analytical Biochemistry 356 (2006) 76-85.*

(Continued)

*Primary Examiner* — David P Porta
*Assistant Examiner* — Djura Malevic
(74) *Attorney, Agent, or Firm* — Locke Lord LLP; Tim Tingkang Xia, Esq.

(57) ABSTRACT

A method for measuring radiation intensity includes measuring the radiation intensity received by the protein in a radiation field based on degree of protein degradation in the radiation field, wherein the degree of degradation is a ratio of the molecular weight of the protein before and after irradiation. The measuring method is simple in operation, small in number of steps, small in error, and capable of measuring radiation doses of various radiation fields or even mixed radiation fields. Use of a biological dosimeter for measuring the radiation intensity by the method in a neutron capture therapy system can not only assess radiation contamination in the irradiation chamber, but also evaluate the neutron dose.

16 Claims, 3 Drawing Sheets

(56) References Cited

U.S. PATENT DOCUMENTS

| | | | | |
|---|---|---|---|---|
| 5,015,855 A * | 5/1991 | Braunlich | G01T 1/105 | 250/DIG. 2 |
| 5,567,936 A * | 10/1996 | Basso | G01T 1/40 | 250/252.1 |
| 9,309,315 B2 * | 4/2016 | Parren | A61P 17/14 | |
| 10,041,057 B2 * | 8/2018 | Gomelsky | C12N 15/62 | |
| 10,157,693 B2 * | 12/2018 | Liu | A61N 5/10 | |
| 10,379,227 B2 * | 8/2019 | Liu | G01T 3/00 | |
| 10,828,513 B2 * | 11/2020 | Friedman | A61N 5/00 | |
| 11,027,152 B1 * | 6/2021 | Friedman | A61N 5/1064 | |
| 11,337,994 B2 * | 5/2022 | Ghandehari | A61K 9/0019 | |
| 2002/0182254 A1 * | 12/2002 | Calias | A61K 38/09 | 424/94.1 |
| 2005/0147555 A1 * | 7/2005 | Fan | C07K 7/08 | 424/9.34 |
| 2006/0257377 A1 * | 11/2006 | Atala | A61L 27/3826 | 424/93.7 |
| 2007/0178521 A1 * | 8/2007 | Sakaino | B01L 3/502753 | 435/7.1 |
| 2008/0283763 A1 * | 11/2008 | Tatsuka | G01N 33/68 | 250/389 |
| 2008/0319375 A1 * | 12/2008 | Hardy | B82Y 5/00 | 600/431 |
| 2009/0136444 A1 * | 5/2009 | Priest | A61P 19/00 | 536/23.4 |
| 2009/0155267 A1 * | 6/2009 | Priest | A61P 35/04 | 424/134.1 |
| 2010/0137144 A1 * | 6/2010 | Remacle | C12Q 1/485 | 506/7 |
| 2011/0003974 A1 * | 1/2011 | Lukyanov | C07K 14/43504 | 435/320.1 |
| 2011/0177084 A1 * | 7/2011 | Saito | A61K 31/7105 | 424/139.1 |
| 2013/0112885 A1 * | 5/2013 | Takahashi | G21K 4/00 | 250/367 |
| 2013/0181137 A1 * | 7/2013 | Watanabe | C09K 11/7734 | 250/369 |
| 2013/0193316 A1 * | 8/2013 | Micke | G01T 1/08 | 250/252.1 |
| 2013/0227718 A1 * | 8/2013 | Matsuda | G01N 21/6486 | 536/23.4 |
| 2013/0243722 A1 * | 9/2013 | Basile | A61P 17/00 | 424/85.2 |
| 2014/0031285 A1 * | 1/2014 | Anseth | C08F 220/365 | 514/8.9 |
| 2014/0099697 A1 * | 4/2014 | Scholz | C07K 1/113 | 530/391.1 |
| 2014/0110601 A1 * | 4/2014 | Liu | G01T 3/00 | 250/474.1 |
| 2014/0221613 A1 * | 8/2014 | Honda | C12N 15/62 | 435/254.2 |
| 2015/0080802 A1 * | 3/2015 | Kang | A61M 37/0015 | 604/173 |
| 2015/0099918 A1 * | 4/2015 | Takayanagi | G01T 1/29 | 702/89 |
| 2015/0366243 A1 * | 12/2015 | Ding | A61K 8/67 | 426/573 |
| 2015/0377906 A1 * | 12/2015 | Wyrobek | G01N 21/00 | 702/19 |
| 2016/0200972 A1 * | 7/2016 | Dorenbos | C09K 11/7772 | 156/242 |
| 2017/0081652 A1 * | 3/2017 | Gomelsky | C12N 9/6472 | |
| 2017/0157424 A1 * | 6/2017 | Zwart | A61N 5/1043 | |
| 2017/0360727 A1 * | 12/2017 | Kim | A61K 39/39558 | |
| 2018/0103852 A1 * | 4/2018 | Dagdeviren | A61B 5/444 | |
| 2018/0120334 A1 * | 5/2018 | Desai | A61K 31/52 | |
| 2018/0233246 A1 * | 8/2018 | Liu | A61N 5/10 | |
| 2018/0277278 A1 * | 9/2018 | Liu | A61N 5/1031 | |
| 2022/0153875 A1 * | 5/2022 | Mizuno | C07K 16/2818 | |

FOREIGN PATENT DOCUMENTS

| | | |
|---|---|---|
| CN | 102508283 A | 6/2012 |
| CN | 103344766 A | 10/2013 |
| CN | 106601320 A | 4/2017 |
| JP | S63229386 A | 9/1988 |

OTHER PUBLICATIONS

International Search Report of PCT/CN2018/100729, dated Nov. 8, 2018.

* cited by examiner

Degree of protein degradation

Degree of protein degradation

METHOD FOR MEASURING RADIATION INTENSITY

RELATED APPLICATION INFORMATION

This application is a continuation of International Application No. PCT/CN2018/100729, filed on Aug. 16, 2018, which claims priority to Chinese Patent Application No. 201710710968.7, filed on Aug. 18, 2017, the disclosures of which are hereby incorporated by reference.

FIELD OF THE DISCLOSURE

The present disclosure relates to the field of radiation, in particular, to a method for measuring radiation intensity; and to a biological dosimeter for measuring radiation intensity by the method, and a neutron capture therapy system with a biological dosimeter.

BACKGROUND OF THE DISCLOSURE

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

With development of science and technology, nuclear technology has been widely used in various fields such as medicine, industry, agriculture, etc. Nuclear technology has a certain risk of nuclear leakage while benefiting human beings, which harms public health and pollutes surrounding environment. Therefore, it is needed to determine the radiation dose in the environment to further assess impact of radiation dose on humans or the environment and to take certain control measures against the radiation dose in the environment.

Use of neutron capture therapy has gradually increased in recent years as an effective means of treating cancer, with boron neutron capture therapy being the most common. Neutrons that are used for boron neutron capture therapy can be supplied by a nuclear reactor or accelerator, with a compound containing $^{10}B$ accumulating at the lesion, and the neutron and $^{10}B$-containing compound react as follows:

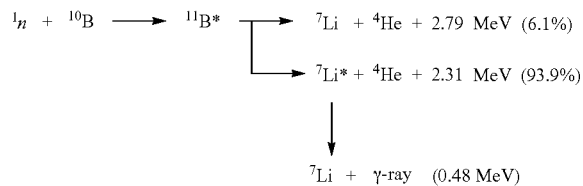

The energy produced by this reaction destroys the lesion for therapeutic purposes. In the course of disease treatment using BNCT technology, if the neutron dose is too low, the boron-containing compound of the lesion cannot fully react with the neutron, and the patient needs to receive radiation for a longer period of time. Excessive neutron doses are often accompanied by contamination by gamma rays or other sources of radiation, posing a threat to safety of patients or health care workers. Therefore, it is needed to pre-evaluate the radiation dose received by the patient prior to neutron irradiation to complete the treatment of the patient with minimal radiation damage.

Currently known biological dosimeters mainly use the influence of radiation on RNA transcription or protein expression to measure the dose received by biomolecules, but these techniques usually require a series of complicated steps such as cell culture, protein separation, calculation, etc., which are complicated and easily bring errors.

SUMMARY

In order to provide a biological dosimeter that is simple in procedure, simple in operation, and capable of accurately measuring radiation dose, one aspect of the present disclosure provides a biological dosimeter that measures the dose received by the protein in the radiation field based on the degree of protein degradation in the radiation field.

Implementations of this aspect may include one or more of the following features.

The degree of protein degradation can be measured by viscosity method, gel filtration chromatography, gel permeation chromatography, gel electrophoresis, light scattering, electrospray ionization mass spectrometry (ESI-MS) or matrix-assisted laser desorption ionization mass spectrometry (MALDI-MS) or other methods for determining molecular weight of protein according to those skilled in the art to measure the molecular weight of the protein before and after irradiation with radiation.

Preferably, in the biological dosimeter, the molecular weight of the protein before and after irradiation with radiation is measured by SDS-gel electrophoresis and the degree of protein degradation after irradiation with radiation is calculated.

In an embodiment of the present disclosure, the degree of protein degradation is quantified by the ratio of the molecular weight of the protein after irradiation with radiation to the molecular weight of the protein before irradiation with radiation.

Preferably, in the biological dosimeter, the radiation field comprises a gamma radiation field, a proton radiation field, a heavy ion radiation field or a mixed radiation field of neutron and gamma.

The biological dosimeter performs measurement of the radiation dose by the following steps.

1) a step of drawing a standard curve: plotting a standard curve of the radiation dose and the degree of protein degradation, and then substituting the degree of protein degradation in the radiation field to be measured into a function corresponding to the standard curve to obtain radiation dose received by the protein in the radiation field to be measured. It should be noted that the radiation dose calculated by the standard curve is the dose of the protein in the radiation field used to draw the standard curve. When the radiation field to be measured is different from the radiation field used to draw the standard curve, it is needed to convert the dose value calculated by the standard curve into the dose of the radiation field to be actually used. The specific operation needs to calculate the coefficient of the radiation dose conversion of two different types of radiation fields through experiments, and then convert the calculated radiation dose into the dose of the radiation field actually used according to the coefficient.

For example, multiple sets of proteins can be used to receive different doses of gamma ray irradiation in the gamma radiation field, and the molecular weights before and after irradiation and the received radiation doses of the proteins after different doses of gamma ray irradiation can be measured and calculated, wherein when a standard curve is drawn, the radiation dose received by the protein in the gamma radiation field is measured with a radiation film (e.g., Radiochromic film or alanine), then the standard curve is drawn and fitted.

2) a step of measuring the dose of the radiation field to be measured: formulating a protein solution having the same concentration as the above step, placing the protein solution in a gamma radiation field, a proton radiation field, a heavy ion radiation field, or a mixed radiation field of neutron and gamma of unknown intensity (to be measured) for receiving radiation, after irradiation, measuring the molecular weight of the protein before and after irradiation, calculating the degree of degradation, and substituting a numerical value representing the degree of protein degradation into the above-mentioned standard curve, and calculating the radiation dose received by the protein in the radiation field to be measured. The dose is expressed by gamma ray. When the radiation field to be measured is a gamma radiation field, the radiation dose can be considered as the actual dose that the protein receives in the gamma radiation. When the radiation field to be measured is a proton radiation field, it is needed to calculate the coefficient of intensity conversion between the gamma ray and the proton radiation ray, and further calculate the actual dose that the protein receives in the proton radiation field during the irradiation time. By the same principle, a standard curve drawn from a protein in a gamma radiation field can also be used to measure the radiation dose of other types of radiation fields.

It is further preferred that in the biological dosimeter, when the dose of the radiation field to be measured is less than 1000 Gy, the protein is selected from radiation sensitive proteins.

The radiation sensitive protein is a protein having a ratio of molecular weight after irradiation to molecular weight of the protein before irradiation of less than 0.8 at a concentration of less than 1 g/L when exposed to a radiation dose of 1000 Gy. The radiation sensitive proteins include, but are not limited to, bovine serum albumin (BSA), ovalbumin, catalase, and transferrin.

It should be noted that the radiation dose that the biological dosimeter provided by an embodiment of the present disclosure can measure is not limited to less than 1000 Gy. When the radiation dose to be measured is higher than 1000 Gy, a protein having different sensitivity to the radiation may be selected according to the radiation intensity of the specific radiation field to be measured. When it is needed to measure the radiation filed with a radiation dose from 1000 Gy to 8000 Gy, the degree of degradation of casein in the radiation field can be used to measure the specific radiation dose, wherein casein has a higher stability in the radiation field relative to bovine serum albumin.

Preferably, casein is used as a biological dosimeter to measure the radiation dose in the radiation field when the dose of radiation to be measured is above 1000 Gy.

Preferably, in the biological dosimeter, the protein is a bovine serum albumin solution having a concentration of 0.2 g/L to 0.6 g/L.

An embodiment of the present disclosure found that the protein with low concentration has good sensitivity in the radiation field, and the degree of protein degradation has a good linear relationship with the radiation field intensity.

Still more preferably, in the biological dosimeter, the bovine serum albumin solution of 0.2 g/L to 0.6 g/L is used to measure a radiation dose of 100 Gy to 500 Gy.

The biological dosimeter composed of low concentration (for example, a concentration less than 1 g/L) protein provided by the embodiment of the present disclosure has high sensitivity and accuracy when measuring the radiation field of low dose. When it is needed to measure the radiation field with high radiation intensity, it is also possible to draw a standard curve using a protein solution with a concentration higher than 1 g/L; or when a low concentration of protein is used as a biological dose timer, the low concentration protein receives short-term irradiation in a high intensity radiation field. It is well known to those skilled in the art that in a radiation field of constant intensity, the longer the irradiation time is, the more radiation dose the protein receives. Conversely, the shorter the irradiation time is, the less radiation dose the protein receives. Therefore, the radiation dose received by the protein can be reduced by changing the irradiation time of the protein in the radiation field, and the standard curve drawn by the low concentration of the protein can be utilized to improve the sensitivity of the dose measurement.

Another aspect of the disclosure provides a method of using the biological dosimeter, the biological dosimeter performs the measurement of the radiation dose by the following steps:

a step of drawing a standard curve: formulating a plurality of sets of protein solutions, respectively placing the protein solutions in the radiation field and exposing them to radiation of different doses, terminating the radiation, measuring the radiation dose received by each group of protein solutions and analyzing the degree of protein degradation after exposure to radiation, and plotting and fitting a standard curve of radiation dose and degree of protein degradation.

a step of measuring the dose of the radiation field to be measured: formulating a protein solution of the same concentration as in the above step, placing the protein solution in a radiation environment to be measured for receiving radiation, terminating radiation and measuring the degree of protein degradation after irradiation, and calculating the radiation intensity received by the protein during the irradiation of the radiation by the standard curve, and substituting a numerical value capable of reflecting the degree of protein degradation into the above standard curve to calculate the radiation dose that the protein receives during the irradiation of the radiation.

Preferably, in the use method, when the radiation dose calculated by the step of measuring the dose of the radiation field to be measured is not within the range of the radiation dose used in drawing the standard curve, the time during which the protein solution is exposed to the radiation can be adjusted in the step of measuring the dose of the radiation field to be measured, so that the radiation dose received by the protein solution is within the range of the radiation dose used in drawing the standard curve, thereby improving accuracy of measuring the dose of the radiation field to be measured.

Further preferably, in the use method, the protein solution is a bovine serum albumin solution having a concentration of 0.2 g/L to 0.6 g/L.

In a third aspect of the present disclosure, in order to measure neutron intensity during neutron capture therapy, a neutron capture therapy system is provided, comprising: a neutron source, a beam shaping assembly, a collimator, and any of the biological dosimeters described above, wherein the neutron source is used to generate a neutron beam, the beam shaping assembly is located at the rear of the neutron source and adjusts the fast neutrons in the neutron beam with a broad energy spectrum generated by the neutron source to epithermal neutrons, the collimator is located at the rear of the beam shaping assembly for converging the epithermal neutrons and irradiating the epithermal neutron beam to a specific spatial position for precise treatment, and the biological dosimeter is used to measure the radiation dose at the location of the biological dosimeter at the rear of the collimator. Wherein, the epithermal neutron energy region is between 0.5 eV and 40 keV, and the fast neutron energy region is greater than 40 keV.

Preferably, in the neutron capture therapy system, the biological dosimeter is located at a specific spatial position to which the epithermal neutron beam is irradiated, and the radiation dose to be received may be measured before the neutron capture therapy is performed on the patient. The radiation dose in the irradiation chamber can also be monitored during the neutron capture therapy.

It is further preferred that in the neutron capture therapy system, the neutron source is an accelerator neutron source or a reactor neutron source.

Still more preferably, in the neutron capture therapy system, the beam shaping assembly comprises a reflector and a moderator, wherein the reflector surrounds the moderator for reflecting neutrons diffused outside the beam shaping assembly back to the moderator, and the moderator is used to moderating fast neutrons into epithermal neutrons.

The biological dosimeter provided by the embodiment of the present disclosure measures the radiation dose of a radiation field with unknown intensity by using the degree of protein degradation in the radiation field to further evaluate or regulate the radiation intensity field intensity. The biological dosimeter provided by the embodiment of the present disclosure has high sensitivity and simple operation, and can be used for estimating and adjusting the neutron dose in the neutron capture therapy system, in addition to being able to detect low dose radiation leakage in the environment.

Further areas of applicability will become apparent from the description provided herein. It should be understood that the description and specific examples are intended for purposes of illustration only and are not intended to limit the scope of the present disclosure.

In a fourth aspect of the present disclosure, a method for measuring radiation intensity is provided, comprising: measuring the radiation intensity received by a protein in a radiation field based on degree of protein degradation in the radiation field, wherein the degree of degradation is a ratio of the molecular weight of the protein before and after irradiation.

Preferably, the method further comprising: formulating a plurality of sets of protein solutions of the same concentration, respectively. placing the protein solutions in a radiation field and exposing them to radiation of different intensities, terminating the radiation, and measuring the radiation intensity received by each group of protein solutions and analyzing the degree of protein degradation after irradiation, and plotting and fitting a standard curve of radiation intensity and degree of protein degradation. The protein is a radiation sensitive protein when the radiation intensity for measurement is less than 1000 Gy, and the radiation sensitive protein is a protein having a ratio of the molecular weight after irradiation to the molecular weight of the protein before irradiation of less than 0.8 at a concentration of less than 1 g/L when exposed to a radiation intensity of 1000 Gy.

Preferably, the protein is a bovine serum albumin solution having a concentration of 0.2 g/L to 0.6 g/L when the radiation intensity for measurement is 100 Gy to 500 Gy.

Preferably, the method further comprising: formulating a protein solution of the same concentration, placing the protein solution in a radiation environment to be measured for receiving radiation, terminating radiation and measuring the degree of protein degradation after irradiation, and calculating the radiation intensity received by the protein during the irradiation of the radiation by the standard curve.

Preferably, the step of placing the protein solution in the radiation environment to be measured for receiving radiation further comprises: adjusting the time during which the protein solution is subjected to radiation exposure such that the radiation intensity received by the protein solution is in the range of the radiation intensity used in the standard curve.

Preferably, the radiation field comprises: a gamma radiation field, a proton radiation field, a heavy ion radiation field, or a mixed radiation field of neutron and gamma.

Preferably, when the radiation field is a mixed radiation field of neutron and gamma, the method further comprises: utilizing the degree of protein degradation in the gamma radiation field to draw a standard curve and calculating the radiation intensity corresponding to the degree of protein degradation $X_i$ as the relative radiation intensity of the protein in the gamma radiation field $D_i = M_j + N_j$, wherein $M_j$ is gamma intensity, $N_j$ is equivalent intensity of neutron relative to gamma, the neutron intensity actually received by the protein is ratio of the equivalent intensity of neutron relative to gamma to the conversion coefficient $K_i$ at the protein degradation concentration, and the conversion coefficient $K_i$ is ratio of the gamma intensity to the neutron intensity at a particular degree of protein degradation.

Preferably, the method for measuring radiation intensity, comprising: measuring the radiation intensity received by a protein in a radiation field based on degree of protein degradation in the radiation field, wherein the degree of degradation is a ratio of the molecular weight of the protein before and after irradiation, wherein the method is provided in a biological dosimeter for measuring radiation dose of a protein.

Preferably, when the radiation dose for measurement is 100 Gy to 500 Gy, the protein used is a bovine serum albumin solution at a concentration of 0.2 g/L to 0.6 g/L.

Preferably, the bovine serum albumin solution of 0.2 g/L to 0.6 g/L is configured to measure a radiation dose of 100 Gy to 500 Gy.

Preferably, the radiation field comprises a gamma radiation field, a proton radiation field, a heavy ion radiation field or a mixed radiation field of neutron and gamma.

Preferably, the molecular weight of the protein before and after irradiation with radiation is measured by SDS-gel electrophoresis and the degree of protein degradation after irradiation with radiation is calculated.

Preferably, the degree of protein degradation is quantified by the ratio of the molecular weight of the protein after irradiation with radiation to the molecular weight of the protein before irradiation with radiation.

Preferably, the radiation field comprises a gamma radiation field, a proton radiation field, a heavy ion radiation field or a mixed radiation field of neutron and gamma.

Preferably, the biological dosimeter performs measurement of the radiation dose by the following steps: formulating a plurality of sets of protein solutions, respectively placing the protein solutions in the radiation field and exposing them to radiation of different doses, terminating the radiation, measuring the radiation dose received by each group of protein solutions and analyzing the degree of protein degradation after exposure to radiation, and plotting and fitting a standard curve of radiation dose and degree of protein degradation; and formulating a protein solution of the same concentration as in the above step, placing the protein solution in a radiation environment to be measured for receiving radiation, terminating radiation and measuring the degree of protein degradation after irradiation, and calculating the radiation intensity received by the protein during the irradiation of the radiation by the standard curve, and substituting a numerical value capable of reflecting the degree of protein degradation into the above standard curve to calculate the radiation dose that the protein receives during the irradiation of the radiation.

Preferably, the method for measuring radiation intensity, comprising: measuring the radiation intensity received by a protein in a radiation field based on degree of protein degradation in the radiation field, wherein the degree of degradation is a ratio of the molecular weight of the protein before and after irradiation, wherein the method is provided in a biological dosimeter in a neutron capture therapy system, wherein the neutron capture therapy system comprises: a neutron source configured to generate a neutron beam, a beam shaping assembly located at the rear of the neutron source for adjusting the fast neutrons in the neutron beam with a broad energy spectrum generated by the neutron source to epithermal neutrons, a collimator located at the rear of the beam shaping assembly for converging the epithermal neutrons, and the biological dosimeter disposed at the rear of the collimator for measuring the radiation dose at the location of the biological dosimeter.

Preferably, the neutron source is an accelerator neutron source or a reactor neutron source.

Preferably, the beam shaping assembly comprises a reflector and a moderator, wherein the reflector surrounds the moderator for reflecting neutrons diffused outside the beam shaping assembly back to the moderator, and the moderator is used to moderating fast neutrons into epithermal neutrons.

Preferably, the epithermal neutron energy region is between 0.5 eV and 40 keV, and the fast neutron energy region is greater than 40 keV.

DETAILED DESCRIPTION

Figure 1:
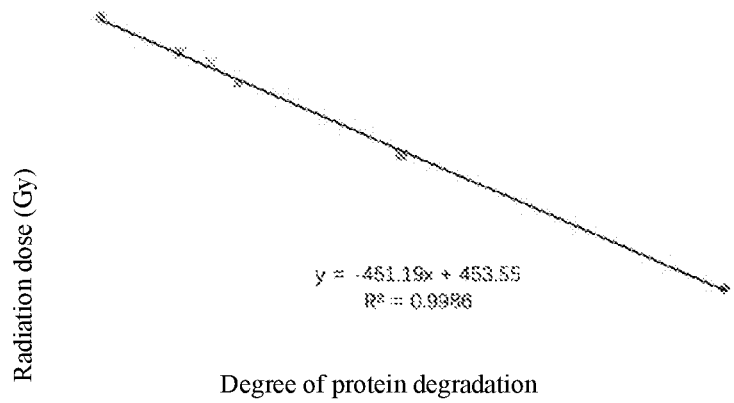
FIG. 1 is a standard curve of a bovine serum albumin solution at a concentration of 0.3 g/L in a gamma radiation field.

The present disclosure will be further described in detail below with reference to the accompanying drawings, so that those skilled in the art can follow the instructions to implement the present disclosure. The above description and the following detailed description are to be considered as illustrative and not restrictive to the subject matter of the present disclosure.

It is to be understood that the terms "having", "comprising" and "including" do not exclude the presence or addition of one or more other components or combinations thereof.

In order to clearly illustrate the technical solution of the present disclosure, the terms present in the present disclosure are defined as follows:

The degree of protein degradation is the ratio of the molecular weight of the protein before and after exposure to radiation;

The numerical value calculated by substituting the value of the degree of protein degradation in the radiation field to be measured into the standard curve is called the radiation dose;

When the radiation field to be measured is different from the radiation field used to draw the standard curve, the radiation dose is called a relative dose:

When the radiation field to be measured and the radiation field used to draw the standard curve belong to the same kind of radiation field, the radiation dose is called the actual dose;

The biological dosimeter provided by the present disclosure can measure the radiation dose of various radiation fields (including mixed radiation fields) by utilizing the degree of degradation of proteins in the radiation field, and the method of using the biological dosimeter comprises two steps;

a step of drawing a standard curve: formulating a plurality of sets of protein solutions, respectively placing the protein solutions in the radiation field and exposing them to radiation of different doses, terminating the radiation, measuring the radiation dose received by each group of protein solutions and analyzing the degree of protein degradation after exposure to radiation, and plotting and fitting a standard curve of radiation dose and degree of protein degradation.

a step of measuring the dose of the radiation field to be measured: formulating a protein solution of the same concentration as in the above step, placing the protein solution in a radiation environment to be measured for receiving radiation, terminating radiation and measuring the degree of protein degradation after irradiation, and calculating the radiation intensity received by the protein during the irradiation of the radiation by the standard curve, and substituting a numerical value capable of reflecting the degree of protein degradation into the standard curve to calculate the radiation dose that the protein receives during the irradiation of the radiation.

Use of the biological dosimeter and drawing of a standard curve of the biological dosimeter will be specifically described below by way of examples with reference to the accompanying drawings:

<Embodiment 1> Drawing of a Standard Curve of a Biological Dosimeter

The standard curve drawn by the biological dosimeter provided by the present disclosure can be drawn according to the degree of protein degradation in any kind of radiation field. In this embodiment, a standard curve is drawn by the degree of degradation of bovine serum albumin in the gamma radiation field to illustrate a method of drawing the standard curve.

Different concentrations of proteins have different degree of degradation in the radiation field. Protein concentration is a factor that affects the degree of degradation in the radiation field. It is further illustrated in the following by the standard curve drawn by the degradation degree of different concentrations of protein in the gamma radiation field.

Drawing of a Standard Curve of a Bovine Serum Albumin Solution at a Concentration of 0.3 g/L in the Gamma Radiation Field:

0.03 g of BSA was dissolved in 100 g of distilled water to formulate a BSA solution having a concentration of 0.3 g/L, and the BSA solution was uniformly mixed and divided into several equal portions, and 6 parts of the BSA solutions were placed in a gamma radiation field to receive different doses of gamma radiation and the dose of each BSA solution in the radiation field was measured by Gafchromic film to be 118 Gy, 258 Gy, 337 Gy, 358 Gy, 370 Gy and 405 Gy.

The molecular weights of the protein without radiation irradiation and the protein exposed to different doses in the radiation field were calculated by SDS-gel electrophoresis in combination with Image J, and the ratio of the molecular weight of the protein after irradiation to the molecular weight of the protein before irradiation is used to describe the degree of protein degradation under the action of the radiation dose. The results are shown in Table 1:

TABLE 1

Degree of degradation of 0.3 g/L bovine serum albumin under different doses of gamma radiation

| Radiation dose received by protein (Gy) | Degree of protein degradation |
|---|---|
| 118 | 0.75 |
| 258 | 0.42 |
| 337 | 0.25 |
| 358 | 0.22 |
| 370 | 0.19 |
| 405 | 0.11 |

From the above experimental data, a function curve between the degree of protein degradation and the radiation dose received by the protein is fitted as shown in FIG. 1. From the fitted standard curve of 0.3 g/L bovine serum albumin shown in FIG. 1, it can be seen that there is a good linear relationship between the degree of protein degradation and its corresponding radiation dose in the range of radiation doses from 118 Gy to 405 Gy.

The same methods and steps were used to calculate the degree of degradation of bovine serum albumin solutions at concentrations of 0.2 g/L, 0.5 g/L, and 0.6 g/L in the gamma radiation field, as shown in Table 2, Table 3, and Table 4, respectively.

TABLE 2

Degree of degradation of 0.2 g/L bovine serum albumin under different doses of gamma radiation

| Radiation dose received by protein (Gy) | Degree of protein degradation |
|---|---|
| 133 | 0.49 |
| 258 | 0.27 |
| 358 | 0.1 |
| 370 | 0.06 |
| 380 | 0.03 |

TABLE 3

Degree of degradation of 0.5 g/L bovine serum albumin under different doses of gamma radiation

| Radiation dose received by protein (Gy) | Degree of protein degradation |
|---|---|
| 142 | 0.85 |
| 258 | 0.49 |
| 324 | 0.31 |
| 383 | 0.15 |

TABLE 4

Degree of degradation of 0.6 g/L bovine serum albumin under different doses of gamma radiation

| Radiation dose received by protein (Gy) | Degree of protein degradation |
|---|---|
| 118 | 0.86 |
| 249 | 0.62 |
| 328 | 0.46 |
| 405 | 0.25 |

TABLE 5

Degree of degradation of 0.1 g/L bovine serum albumin under different doses of gamma radiation

| Radiation dose received by protein (Gy) | Degree of protein degradation |
|---|---|
| 118 | 0.37 |
| 133 | 0.28 |
| 142 | 0.22 |
| 215 | 0.1 |

TABLE 6

Degree of degradation of 1 g/L bovine serum albumin under different doses of gamma radiation

| Radiation dose received by protein (Gy) | Degree of protein degradation |
|---|---|
| 249 | 0.87 |
| 258 | 0.83 |
| 328 | 0.78 |
| 358 | 0.67 |
| 405 | 0.58 |
| 419 | 0.55 |

Figure 2:
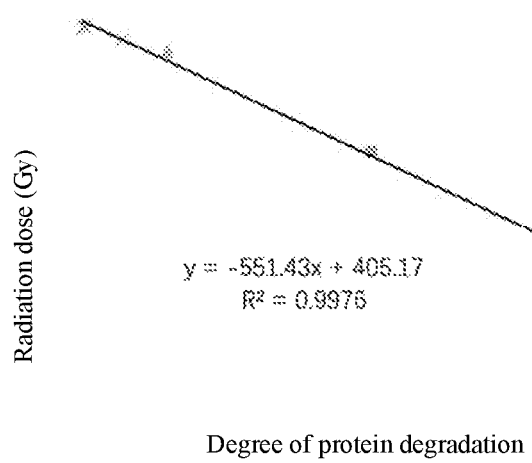
FIG. 2 is a standard curve of a bovine serum albumin solution at a concentration of 0.2 g/L in a gamma radiation field.
Figure 3:
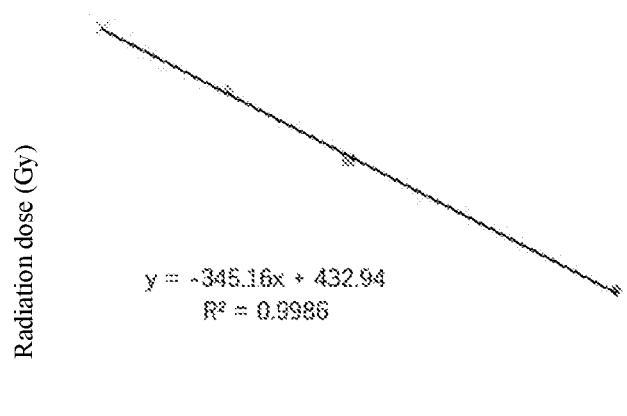
FIG. 3 is a standard curve of a bovine serum albumin solution at a concentration of 0.5 g/L in a gamma radiation field.
Figure 4:
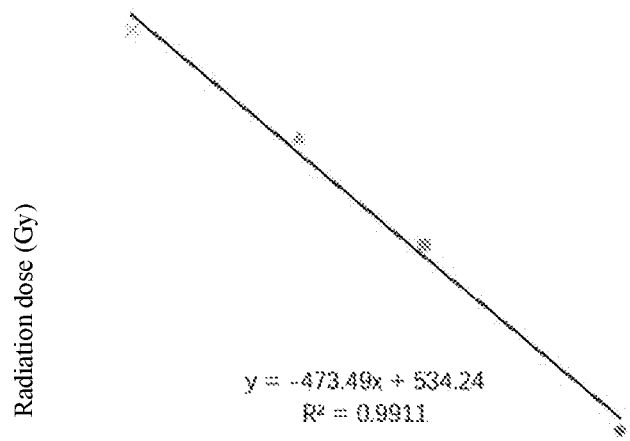
FIG. 4 is a standard curve of a bovine serum albumin solution at a concentration of 0.6 g/L in a gamma radiation field.

According to the experimental data in Tables 2 to 4, the standard curves of the degree of degradation of different concentrations of protein in the radiation field are respectively plotted as shown in FIG. 2 to FIG. 4, and it can be seen from the figures that the degree of degradation of different concentrations of protein in the radiation field has a good linear relationship with the radiation dose it receives.

Tables 5 and 6 show the degradation of bovine serum albumin at concentrations of 0.1 g/L and 1 g/L, respectively, under different doses of gamma radiation. From the data in these two tables, it can be found that the degree of protein degradation in the radiation field has a linear relationship with the radiation dose it receives, indicating that a protein solution with a concentration lower than 0.2 g/L or a protein solution with a concentration higher than 0.6 g/L can also be used as a biological dosimeter.

The standard curve can be used to detect the radiation dose of the same concentration of protein in a radiation field of unknown intensity and unknown type, and the radiation dose calculated by substituting it into the standard curve is expressed by the dose of gamma rays. When the unknown type of radiation field is a gamma radiation field, the calculated radiation dose is the same as the actual radiation dose received by the protein in the radiation field to be measured. When the unknown type of radiation field is not a gamma radiation field, the calculated radiation dose is the relative dose of the protein in the unknown radiation field. It is needed to calculate the conversion coefficient between the gamma radiation field and the radiation field to be measured through experiments.

<Embodiment 2> Method for Measuring Actual Radiation Dose of Mixed Radiation Field of Neutron and Gamma by Biological Dosimeter When measuring the radiation intensity field with a biological dosimeter, the standard curve between the degree of protein degradation and the radiation dose can be determined in advance by the type of radiation field to be measured. It is also possible to measure the actual radiation dose of the radiation field to be measured by using a standard curve determined from a radiation field which is not to be measured and the conversion coefficient between the radiation field to be measured and the radiation field used for the standard curve.

The conversion coefficient between the radiation fields needs to be further confirmed by experiments. In this embodiment, the calculation method of the conversion coefficient between the gamma radiation field and the neutron radiation field is taken as an example to illustrate the calculation method of the conversion coefficient between different radiation fields.

According to <Embodiment 1>, a certain concentration of the protein solution is formulated, and the protein solution is placed in a gamma radiation field to receive different doses ($D\gamma_1$, $D\gamma_2$ ... $D\gamma_n$) of gamma ray irradiation, and the degree of protein degradation $X_1$, $X_2$ ... $X_n$ at the dose of $D\gamma_1$, $D\gamma_2$ ... $D\gamma_n$ was calculated, respectively.

Protein solutions of the above specific concentrations were formulated and placed in a neutron irradiation field for irradiation. When the degree of protein degradation in the neutron radiation field is consistent with the degree of protein degradation in the gamma radiation field (i.e., when the degradation degree of the protein in the neutron radiation field is $X_1$, $X_2$ ... $X_n$, respectively), the neutron doses $Dn_1$, $Dn_2$ ... $Dn_n$ received by the proteins are read.

The ratio of the gamma dose to the neutron dose of the protein at a particular degree of degradation is set as the conversion coefficient between the neutron and gamma for the degree of protein degradation:

$$K_i = D\gamma_i / Dn_i \text{(wherein } i \text{ takes values from 1 to } n\text{)}$$

A curve is drawn between the degree of protein degradation and the conversion coefficient corresponding to the degree of degradation, and the curve function is fitted:

$$Ki = f(Xi)$$

When the relative radiation dose of the protein in the neutron radiation field is calculated by the standard curve made by the gamma radiation field, first, the conversion coefficient at the degree of degradation is calculated according to substituting the degree of protein degradation into the function Ki=f(Xi). Then, the neutron radiation dose actually received by the protein in the neutron radiation field is calculated based on the conversion coefficient and the relative radiation dose calculated from the standard curve. The neutron radiation dose actually received by the protein in the neutron radiation field is a ratio of the relative radiation dose to the conversion coefficient.

The dose received by the protein in the radiation field in this embodiment was measured by Radiochromic film, and can also be measured by other methods known to those skilled in the art which are able to measure the amount of radiation received by the protein at the site of irradiation.

When the radiation field to be measured is a mixed radiation field of neutron and gamma and the standard curve is drawn by the degree of protein degradation in the gamma radiation field, the radiation dose Xi corresponding to a certain degree of protein degradation is calculated by the biological dosimeter is the relative radiation dose $D_i$ of the protein in the gamma radiation field, wherein $D_i = M_j + N_j$. Wherein, $M_j$ is the gamma dose, $N_j$ is the equivalent dose of neutrons relative to gamma, wherein the gamma dose $M_j$ can be calculated by Monte Carlo, and the neutron dose actually received by the protein is the ratio of the equivalent dose of neutrons relative to gamma to the conversion coefficient (Ki) at the protein degradation concentration.

<Embodiment 3> Neutron Capture Therapy System Comprising Biological Dosimeter

The biological dosimeter provided by the embodiment of the present disclosure is used for detecting radiation dose, and can be used not only to detect radiation pollution in the environment, but also to estimate the intensity or dose of the neutron beam in the neutron capture therapy system to guide treatment process.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n)$^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7$Li (p, n) $^7$Be asks for more than $^9$Be (p, n)$^9$B does because of low melting point and poor thermal conductivity coefficient of the metal (lithium) target. In these embodiments of the present disclosure is $^7$Li (p, n) $^7$Be.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux $>1\times10^9$ n/cm$^2$s
Fast neutron contamination $<2\times10^{-13}$ Gy-cm$^2$/n
Photon contamination $<2\times10^{-13}$ Gy-cm$^2$/n
Thermal to epithermal neutron flux ratio $<0.05$
Epithermal neutron current to flux ratio $>0.7$ Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time $<=30$ min (proton current for accelerator is 10 mA)
2. 30.0RBE-Gy treatable depth $>=7$ cm
3. The maximum tumor dose $>=60.0$RBE-Gy
4. The maximum dose of normal brain tissue $<=12.5$RBE-Gy
5. The maximum skin dose $<=11.0$RBE-Gy Note: RBE stands for relative biological effectiveness. Since photons and neutrons express different biological effectiveness, the dose above should be multiplied with RBE of different tissues to obtain equivalent dose.

Figure 5:
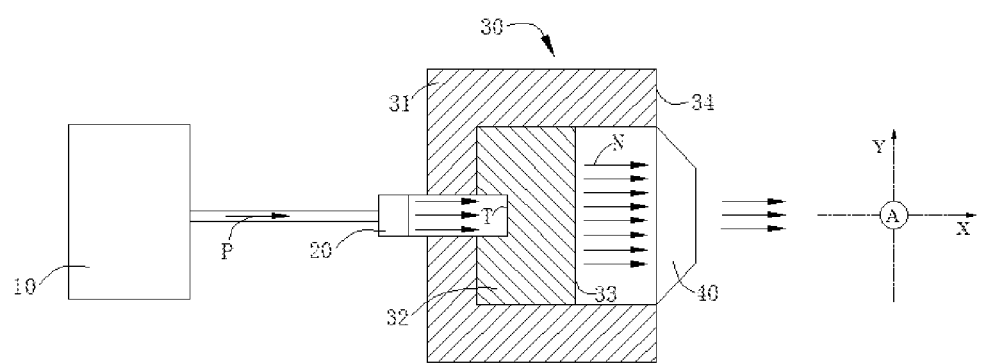
FIG. 5 is a neutron capture therapy system containing a biological dosimeter.

The neutron capture treatment system including the biological dosimeter is further described below with reference to the drawings: the neutron source in the neutron capture treatment system shown in FIG. 5 is an accelerator neutron source, wherein the charged particles generated by the accelerator 10 form a charged particle beam P, the charged particle beam impinges on the target T in the neutron generating device 20 to form a mixed radiation field containing thermal neutrons, fast neutrons, and epithermal neutrons. The mixed radiation field reflects the neutrons diffused to the surroundings back into the mixed radiation field by the reflector 31 in the beam shaping body 30, then retarded by the slow speed body 32, and the thermal neutron absorber 33 absorbs the lower energy thermal neutrons. Thereafter, a neutron beam N mainly composed of superthermal neutrons is formed, and the neutron beam flows are concentrated by the collimator 40 to accurately illuminate the portion to be irradiated of the patient, and further, in order to prevent the radiation in the beam shaping body 30 from diffusing out, a radiation shield 34 is disposed adjacent the beam exit at the rear of the beam shaping body 30.

Preventing radiation from damaging other normal tissues of the body during treatment often requires positioning the patient within the irradiation chamber prior to illuminating the neutron beam. As shown in FIG. 5, before the neutron irradiation, the portion to be irradiated of the patient is pre-positioned according to the direction of the neutron beam passing through the collimator to the intersection of the X-axis and the Y-axis in the neutron beam direction to achieve precise illumination.

In order to evaluate the neutron radiation dose of the neutron beam at the site to be treated of the patient within the irradiation chamber, it is needed to provide a biological dosimeter A at the predetermined position in the irradiation chamber, which is used to measure the radiation dose at the intersection of the X-axis and the Y-axis in the direction of the neutron beam, and the radiation field in which the biological dosimeter is located is a mixed radiation field of neutron and gamma. The dose calculated by the biological dosimeter based on substituting the degree of protein degradation at the intersection into the standard curve is a relative radiation dose of the protein in the radiation filed used to draw the standard curve, and the neutron dose and the gamma dose in the mixed radiation field need to be separately calculated according to the method of <Embodiment 2>.

The biological dosimeter A can be located at other locations in the illumination chamber in addition to the location shown in FIG. 5 for measuring the dose of the radiation field at the location of the biological dosimeter. Since the biological dosimeter is simple and light to use, it can be located at any position in the irradiation chamber to evaluate the radiation dose at the position, and further determine and control the radiation pollution in the irradiation chamber, thereby showing that the biological dosimeter is of great significance in the neutron capture system.

are not limited to the contents described in the above embodiments and the structures represented in the drawings. Any obvious changes, substitutions, or modifications made on the basis of the present disclosure shall be within the scope of protection claimed by the present disclosure.

What is claimed is:

1. A method for measuring radiation intensity, comprising:
   measuring the radiation intensity received by a protein in a radiation field based on degree of protein degradation in the radiation field, wherein the degree of degradation is a ratio of the molecular weight of the protein before and after irradiation;
   wherein the radiation field comprises: a gamma radiation field, a proton radiation field, a heavy ion radiation field, or a mixed radiation field of neutron and gamma;
   wherein when the radiation field is a mixed radiation field of neutron and gamma, the method further comprises: utilizing the degree of protein degradation in the gamma radiation field to draw a standard curve and calculating the radiation intensity corresponding to the degree of protein degradation $X_i$ as the relative radiation intensity of the protein in the gamma radiation field $D_i=M_j+N_j$, wherein $M_j$ is gamma intensity, $N_j$ is equivalent intensity of neutron relative to gamma, the neutron intensity actually received by the protein is ratio of the equivalent intensity of neutron relative to gamma to the conversion coefficient $K_i$ at the protein degradation concentration, and the conversion coefficient $K_i$ is ratio of the gamma intensity to the neutron intensity at a particular degree of protein degradation.

2. The method according to claim 1 further comprising:
   formulating a plurality of sets of protein solutions of the same concentration,
   respectively placing the protein solutions in a radiation field and exposing them to radiation of different intensities,
   terminating the radiation, and measuring the radiation intensity received by each group of protein solutions and analyzing the degree of protein degradation after irradiation, and
   plotting and fitting a standard curve of radiation intensity and degree of protein degradation.

3. The method according to claim 1, wherein the protein is a radiation sensitive protein when the radiation intensity for measurement is less than 1000 Gy, and the radiation sensitive protein is a protein having a ratio of the molecular weight after irradiation to the molecular weight of the protein before irradiation of less than 0.8 at a concentration of less than 1 g/L when exposed to a radiation intensity of 1000 Gy.

4. The method according to claim 1, wherein the protein is a bovine serum albumin solution having a concentration of 0.2 g/L to 0.6 g/L when the radiation intensity for measurement is 100 Gy to 500 Gy.

5. The method according to claim 2 further comprising:
   formulating a protein solution of the same concentration as in claim 2, placing the protein solution in a radiation environment to be measured for receiving radiation, terminating radiation and measuring the degree of protein degradation after irradiation, and calculating the radiation intensity received by the protein during the irradiation of the radiation by the standard curve.

6. The method according to claim 5, wherein the step of placing the protein solution in the radiation environment to be measured for receiving radiation further comprises:
   adjusting the time during which the protein solution is subjected to radiation exposure such that the radiation intensity received by the protein solution is in the range of the radiation intensity used in the standard curve.

7. The method for measuring radiation intensity according to claim 1 for use in a neutron capture therapy system, wherein the method is provided in a biological dosimeter for measuring radiation dose of the protein.

8. The method according to claim 7, wherein when the radiation dose for measurement is 100 Gy to 500 Gy, the protein used is a bovine serum albumin solution at a concentration of 0.2 g/L to 0.6 g/L.

9. The method according to claim 8, wherein the bovine serum albumin solution of 0.2 g/L to 0.6 g/L is configured to measure a radiation dose of 100 Gy to 500 Gy.

10. The method according to claim 7, wherein the molecular weight of the protein before and after irradiation with radiation is measured by SDS-gel electrophoresis and the degree of protein degradation after irradiation with radiation is calculated.

11. The method according to claim 7, wherein the degree of protein degradation is quantified by the ratio of the molecular weight of the protein after irradiation with radiation to the molecular weight of the protein before irradiation with radiation.

12. The method according to claim 7, wherein the biological dosimeter performs measurement of the radiation dose by the following steps:
formulating a plurality of sets of protein solutions, respectively placing the protein solutions in the radiation field and exposing them to radiation of different doses, terminating the radiation, measuring the radiation dose received by each group of protein solutions and analyzing the degree of protein degradation after exposure to radiation, and plotting and fitting a standard curve of radiation dose and degree of protein degradation; and
formulating a protein solution of the same concentration as in the above step, placing the protein solution in a radiation environment to be measured for receiving radiation, terminating radiation and measuring the degree of protein degradation after irradiation, and calculating the radiation intensity received by the protein during the irradiation of the radiation by the standard curve, and substituting a numerical value capable of reflecting the degree of protein degradation into the above standard curve to calculate the radiation dose that the protein receives during the irradiation of the radiation.

13. The method for measuring radiation intensity according to claim 1 for use in a neutron capture therapy system, wherein the method is provided in a biological dosimeter in a neutron capture therapy system, wherein the neutron capture therapy system comprises:
a neutron source configured to generate a neutron beam,
a beam shaping assembly located at the rear of the neutron source for adjusting the fast neutrons in the neutron beam with a broad energy spectrum generated by the neutron source to epithermal neutrons,
a collimator located at the rear of the beam shaping assembly for converging the epithermal neutrons, and
the biological dosimeter disposed at the rear of the collimator for measuring the radiation dose at the location of the biological dosimeter.

14. The method according to claim 13, wherein the neutron source is an accelerator neutron source or a reactor neutron source.

15. The method according to claim 13, wherein the beam shaping assembly comprises a reflector and a moderator, wherein the reflector surrounds the moderator for reflecting neutrons diffused outside the beam shaping assembly back to the moderator, and the moderator is used to moderating fast neutrons into epithermal neutrons.

16. The method according to claim 13, wherein the epithermal neutron energy region is between 0.5 eV and 40 keV, and the fast neutron energy region is greater than 40 keV.

* * * * *